(12) United States Patent
Terentev et al.

(10) Patent No.: US 9,989,666 B2
(45) Date of Patent: Jun. 5, 2018

(54) IMAGING OF EARTH FORMATION WITH HIGH FREQUENCY SENSOR

(71) Applicant: BAKER HUGHES INCORPORATED, Houston, TX (US)

(72) Inventors: Sergey A. Terentev, Omsk (RU); Yuliy Dashevsky, Novosibirsk (RU)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 0 days. days.

(21) Appl. No.: 14/901,614

(22) PCT Filed: Apr. 2, 2014

(86) PCT No.: PCT/RU2014/000238
§ 371 (c)(1),
(2) Date: Dec. 28, 2015

(87) PCT Pub. No.: WO2015/152758
PCT Pub. Date: Oct. 8, 2015

(65) Prior Publication Data
US 2017/0010377 A1    Jan. 12, 2017

(51) Int. Cl.
*G01V 3/00* (2006.01)
*G01V 3/30* (2006.01)
(Continued)

(52) U.S. Cl.
CPC ............ *G01V 3/30* (2013.01); *E21B 49/00* (2013.01); *E21B 49/08* (2013.01);
(Continued)

(58) Field of Classification Search
CPC ....... H01L 21/00; H01L 2221/00; G01N 1/00; G01N 2201/00; G01D 1/00
See application file for complete search history.

(56) References Cited

U.S. PATENT DOCUMENTS 2,863,145 A    12/1958  Turner
3,781,898 A    12/1973  Holloway
(Continued)

FOREIGN PATENT DOCUMENTS

EP    0163574 A2    12/1985
GB    2250098 A     5/1992

OTHER PUBLICATIONS

Ana Maria Yepes, "Multilayer Antenna Arrays for Environmental Sensing Applications"; Georgia Institute of Technology; Presented Aug. 2010; Retrieved from https://smartech.gatech.edu/ on Aug. 9, 2013; 79 pages.
(Continued)

*Primary Examiner* — Jermele M Hollington
*Assistant Examiner* — Temilade Rhodes-Vivour
(74) *Attorney, Agent, or Firm* — Cantor Colburn LLP

(57) ABSTRACT

A method for determining at least one electrical property of an earth formation includes emitting an electromagnetic signal into the earth formation from an antenna and measuring an electromagnetic signal from the earth formation. The antenna is a broadband log antenna mounted on a substrate having at least a high dielectric permittivity, defined as a dielectric permittivity of about $\in=100$ to $\in=1000$ or a gigantic dielectric permittivity, defined as a dielectric permittivity of about $\in=1000$ or greater. The antenna has a radius between about 2.5 millimeters (mm) and 10 centimeters (cm). The method further includes determining at least one electrical property of one or more of a borehole, a borehole fluid, and the earth formation based on measuring the electromagnetic signal.

18 Claims, 3 Drawing Sheets

(51) Int. Cl.
  *E21B 49/00* (2006.01)
  *E21B 49/08* (2006.01)
  *H01L 21/00* (2006.01)
(52) U.S. Cl.
  CPC .......... *G01N 2201/00* (2013.01); *H01L 21/00* (2013.01); *H01L 2221/00* (2013.01)

(56) References Cited

U.S. PATENT DOCUMENTS

| | | | |
|---|---|---|---|
| 3,969,732 A | | 7/1976 | Holloway |
| 4,012,744 A | | 3/1977 | Greiser |
| 4,114,164 A | | 9/1978 | Greiser |
| 4,511,843 A | | 4/1985 | Thoraval |
| 6,046,707 A | | 4/2000 | Gaughan et al. |
| 6,163,155 A | * | 12/2000 | Bittar ................ G01V 3/28 324/338 |
| 6,188,358 B1 | | 2/2001 | Clynne |
| 6,476,609 B1 | * | 11/2002 | Bittar ................ G01V 3/28 175/45 |
| 6,509,880 B2 | | 1/2003 | Sabet et al. |
| 7,289,008 B2 | | 10/2007 | Kuroki et al. |
| 7,750,861 B2 | | 7/2010 | Delgado et al. |
| 2008/0068025 A1 | * | 3/2008 | Gold ................ G01V 3/24 324/367 |
| 2008/0074336 A1 | * | 3/2008 | Signorelli ........... G01V 3/28 343/719 |
| 2009/0051246 A1 | | 2/2009 | Mueller |
| 2009/0135086 A1 | * | 5/2009 | Fuller ................ G01S 7/414 343/909 |
| 2010/0151797 A1 | * | 6/2010 | Viala ................ H01F 10/3218 455/73 |
| 2011/0141847 A1 | * | 6/2011 | Frumin ................ E21B 47/06 367/35 |
| 2011/0221443 A1 | * | 9/2011 | Bittar ................ G01V 3/30 324/339 |
| 2012/0018524 A1 | | 1/2012 | Loi et al. |
| 2012/0019394 A1 | | 1/2012 | Loi |
| 2012/0020183 A1 | | 1/2012 | Loi et al. |
| 2012/0051189 A1 | * | 3/2012 | Signorelli ............ G01V 3/12 367/177 |
| 2012/0223869 A1 | * | 9/2012 | Kim ................ H01Q 9/0442 343/769 |
| 2013/0249762 A1 | * | 9/2013 | Grelier ................ H01Q 9/27 343/834 |

OTHER PUBLICATIONS

Microwave Dielectric Components—Resonators Filters and Patch Antenna, Token Electronics Industry Co., Ltd.; Retrieved from http://www.token.com.tw/pdf/ceramic-discriminator.pdf on Aug. 9, 2013; 32 pages.

Notification of Transmittal of the International Search Report and the Written Opinion of the International Searching Authority, or the Declaration; PCT/RU2014/000238; dated Dec. 5, 2014; 8 pages.

* cited by examiner

IMAGING OF EARTH FORMATION WITH HIGH FREQUENCY SENSOR

CROSS-REFERENCE TO RELATED APPLICATION

This application claims the benefit of priority to PCT Application No. PCT/RU2014/000238 filed Apr. 2, 2014, the disclosure of which is incorporated herein by reference in its entirety.

BACKGROUND

Conventional systems for measuring electrical properties of geological formations tend to use electromagnetic fields of low frequency, due to the high attenuation rate of high frequency electromagnetic fields in conductive media. However, analysis of geological formations using high frequencies would provide additional tools for interpreting the geological formations.

SUMMARY

A method for determining at least one electrical property of an earth formation includes emitting, by a first antenna, an electromagnetic signal into the earth formation and measuring, by a second antenna, an electromagnetic signal from the earth formation. At least one of the first and second antenna being a broadband log antenna mounted on a substrate having a at least a high dielectric permittivity, defined as a dielectric permittivity of about $\in=100$ to about $\in=1000$ or a gigantic dielectric permittivity, defined as a dielectric permittivity of about $\in=1000$ or greater, and the at least one of the first and second antenna having the high dielectric permittivity further having a radius of between about 2.5 millimeters (mm) and about 10 centimeters (cm). The method further includes determining at least one electrical property of one or more of a borehole, a borehole fluid, and the earth formation based on measuring the electromagnetic signal.

A borehole system includes a downhole assembly and a computer. The downhole assembly includes at least one broadband log antenna configured to perform at least one of emitting an electromagnetic signal into the earth formation and measuring an electromagnetic signal from the earth formation. The broadband log antenna is mounted on a substrate having at least a high dielectric permittivity, defined as a dielectric permittivity of about $\in=100$ to about $\in=1000$ or a gigantic dielectric permittivity, defined as a dielectric permittivity of about $\in=1000$ or greater. The broadband log antenna has a radius of between about 2.5 millimeters (mm) and about 10 centimeters (cm). The computer is configured to perform at least one of generating a signal to cause the at least one antenna to emit the electromagnetic signal into the earth formation, and receiving a signal from the antenna based on an electromagnetic signal received by the antenna from the earth formation. The computer is further configured to determine at least one electrical property of one or more of a borehole, a borehole fluid, and the earth formation based on measuring the electromagnetic signal received from the at least one antenna.

BRIEF DESCRIPTION OF THE DRAWINGS

Referring now to the drawings wherein like elements are numbered alike in the several Figures.

DETAILED DESCRIPTION

Imaging of earth formation at high frequencies provides information unavailable at lower frequencies. Embodiments of the invention relate to a system and method of analyzing earth formations using a sensor having a very-high-dielectric substrate.

Figure 1A:
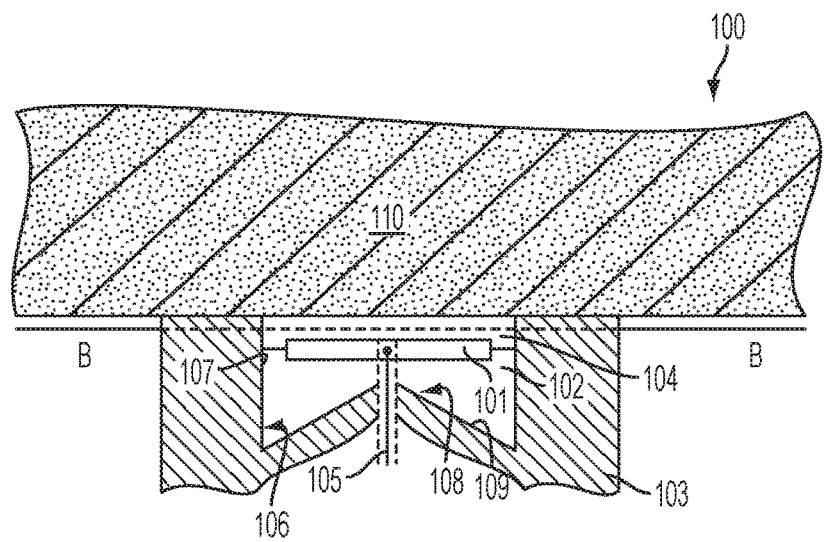
FIG. 1A illustrates a sensor system 100 according to an embodiment of the invention.

FIG. 1A illustrates a sensor system 100 according to an embodiment of the invention. The system 100 includes an antenna 101 on a high-dielectric-permittivity substrate 102. The antenna 101 and substrate 102 are located in a cavity in a housing 103, such as a metal downhole segment, which may be part of downhole piping or tubing, wireline assembly, drill string assembly, drill bit, or any other downhole equipment located in a borehole in an earth formation 110. A cover 104 is located between the antenna 101 and an earth formation 110. In one embodiment, the cover 104 is selected to have a relatively low dielectric constant relative to the substrate 102. A wire 105 is connected to the antenna 101 to transmit signals to the antenna 101, to receive signals from the antenna 101, or both.

An absorber layer 106 is formed on side walls 107 of the cavity formed by the housing 103, and a reflector layer 108 is formed on a rear wall 109 of the cavity formed by the housing 103. For purposes of description, a side of the cavity next to the earth formation 110 is defined as a "front" of the cavity and a side of the cavity farthest from the earth formation 110 is defined as the "rear" of the cavity. It is understood that the housing 103 and system 100 may have any orientation with respect to the earth formation 110.

In one embodiment, the rear wall 109 of the cavity has a conical shape, having a peak around a center of the cavity and sloping from the peak to the side walls 107. In another embodiment, the rear wall 109 is substantially flat. Embodiments of the invention encompass a rear wall 109 having any shape.

In embodiments of the invention, a high-dielectric-permittivity substrate 102 is a ceramic. In one embodiment, the high-dielectric-permittivity is defined as a permittivity greater than about $\in=1\cdot10^2$. In one embodiment, the permittivity of the high-dielectric-permittivity substrate 102 is in a range from about $\in=2\cdot10^2$ to about $\in=2\cdot10^4$. In one embodiment, a dielectric permittivity of the earth formation 110 is determined, and the permittivity of the substrate 102 is selected to be at least as high as the dielectric permittivity of the earth formation 110, such as a portion of the earth formation adjacent to the housing 103 and cover 104. In one embodiment, the permittivity of the high-dielectric-permittivity substrate 102 is selected to be higher than the dielectric permittivity of the earth formation 110.

Figure 1B:
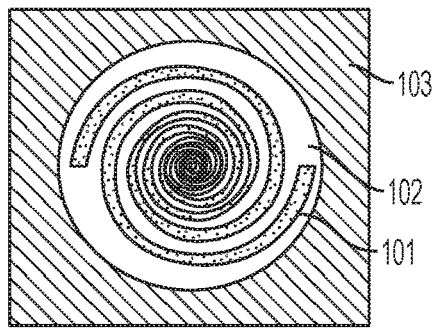
FIG. 1B illustrates a cross-section of the system 100 along the line B-B of FIG. 1A.

FIG. 1B illustrates a cross-section of the system 100 along the line B-B of FIG. 1A, with the cover 104 removed. As illustrated in FIG. 1B, in one embodiment, the antenna 101 is a log-periodic spiral antenna. However, embodiments of the invention encompass any antenna capable of being mounted on a high-dielectric-permittivity substrate 102. In one embodiment, the antenna 101 is a broadband antenna, or an antenna capable of operating simultaneously over a broad range of frequencies.

In the present specification and claims, and in the art, a non-broadband antenna is an antenna which operates at a single frequency or over a very narrow band of frequencies. In contrast, a broadband antenna is an antenna which operates satisfactorily over a wide range of frequencies, such as for all twelve very high frequency television channels. In operation, the broadband capability of embodiments of the present invention allows for frequency sounding of a formation and obtaining inhomogeneous formations at different depths. In other words, the broadband antenna allows for imaging of the formation and studying dispersive properties of the formation.

In embodiments of the invention, the range of frequencies may be in the tens of Herz, in the hundreds of Herz, or in the GigaHerz range. In embodiments of the invention, the high-dielectric-permittivity substrate 102 allows for an antenna 101 of a small size. The permittivity of the high-dielectric-permittivity substrate 102 and the size of the antenna 101 are together selected to generate and/or detect electromagnetic signals at a predetermined frequency.

In one embodiment, the dielectric permittivity of the substrate 102 and the size of the antenna 101 are selected to transmit and/or receive a frequency between about 120 MHz and about 2.5 GHz. In another embodiment, the dielectric permittivity of the substrate 102 and the size of the antenna 101 are selected to transmit and/or receive a frequency between about 12 MHz and about 240 MHz. In one embodiment, the dielectric permittivity of the substrate 102 and the size of the antenna 101 are selected to detect both electric conductivity and dielectric permittivity of an earth formation. In one embodiment, the dielectric permittivity of the substrate 102 and the size of the antenna 101 are selected to allow for a resonance operating mode. Resonance mode is a state of operation at which the system, including the antenna, is working at a peak efficiency. When transmitting, energy is sent from a transmitter along a feedline to an antenna. The antenna then converts this energy into electromagnetic energy which is radiated into the surrounding medium, including a borehole and earth formation. If the antenna and feedline are not working at peak efficiency some of this energy is reflected back to the transmitter along the feedline. This reflection should be avoided because reflected power contributes nothing to the transmitted signal, and it is essentially a waste of energy. Thus, the resonance mode is a mode of operation in which the entire system is working at a peak efficiency and is implemented by modeling to choose proper frequencies, dimensions of the antenna, etc.

In one embodiment, the dielectric permittivity of the substrate 102 is selected such that the antenna 101 is configured to transmit and/or receive signals at a frequency between about 10 MHz and about 30 GHz, and a size of the antenna 101 is such that one of a diameter, height, and width of the antenna 101 is between about 0.5 cm and about 10 cm. In one embodiment, the dielectric permittivity of the ceramic 102 is selected such that the antenna 101 has a broadband frequency sub-band of between about 10 MHz to about 30 GHz.

Figure 2:
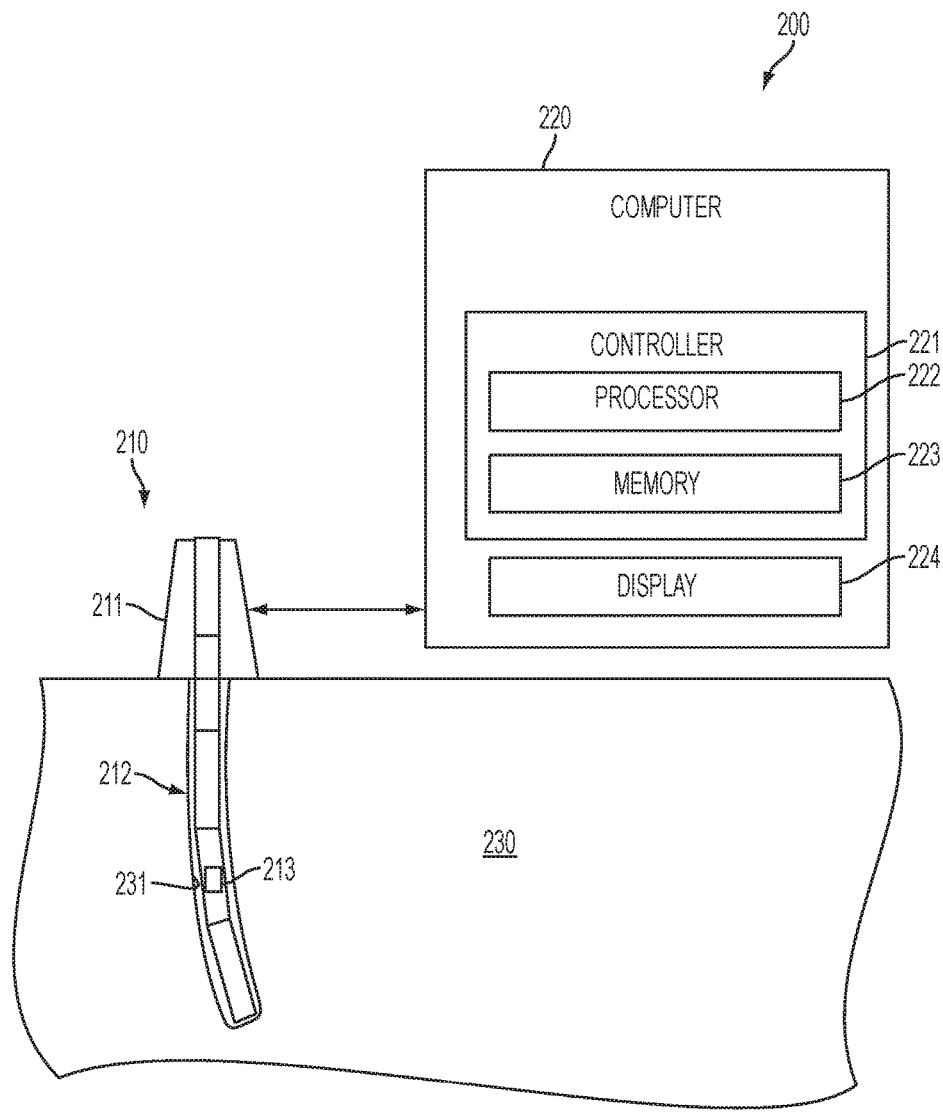
FIG. 2 illustrates a borehole system including the sensor system according to an embodiment of the invention.

FIG. 2 illustrates a borehole system 200 according to an embodiment of the invention. The system 200 includes a downhole assembly 210 and computer 220. The downhole assembly 210 includes a derrick 211 and downhole portion 212 located in a borehole 231 in an earth formation 230. The downhole portion includes an antenna 213, which corresponds to the antenna 101 illustrated in FIGS. 1A and 1B. The downhole portion may be a pipe, drill string, drill bit, wireline assembly, or any other downhole structure configured to be inserted in the borehole 231.

The computer 220 includes a controller 221 including processor 222 and memory 223, and a display 224. The controller 221 is configured to perform one or both of controlling the antenna 213 to generate an electromagnetic signal or field and receiving signals from the antenna 213 based on received or detected electromagnetic signals. The controller 221 generates display data, such as 3D display data, based on the signals received from the antenna 213 to generate a display of one or more of the borehole 231 and the earth formation 230.

In one embodiment, the antenna 213 includes an array of antennae. In one embodiment, the array of antennae include a transmitting array to transmit electromagnetic signals into the earth formation 230 and a receiving array to receive electromagnetic signals from the earth formation 230.

In one embodiment of the invention, a miniature broadband spiral antennae, for example a log-periodic antenna, is used to perform imaging in an earth formation. To address the contradictory requirements of lowering the frequency domain of the sensor to the range between tens MHz to tens of GHz and reducing the sensor size to several centimeters, the antenna is mounted on a ceramic substrate having a very high dielectric permittivity. In some embodiments, a set of broadband sensors are used as transmitters and receivers to transform the signals being measured into an image of the medium being measured at different distances away from a wellbore wall to achieve three-dimensional (3D) imaging.

An antenna according to embodiments of the invention may be designed based on the following formula:

$$r_0^1 \approx \frac{1}{\omega}\sqrt{\frac{2}{\varepsilon_2 \varepsilon_0 \mu_0}} \quad (1)$$

In the above equation (1), r represents the radius of a resonant hoop, or of the conductive spiral portion of the antenna, omega represents a frequency, epsilon2 represents a dielectric permittivity of a substrate on which the antenna is mounted, epsilon0 represents the dielectric permittivity of air, and mu0 represents the magnetic permittivity of air. As illustrated in equation (1), as the dielectric permittivity of the antenna substrate increases, an operating frequency of the antenna will decrease.

Figure 3:
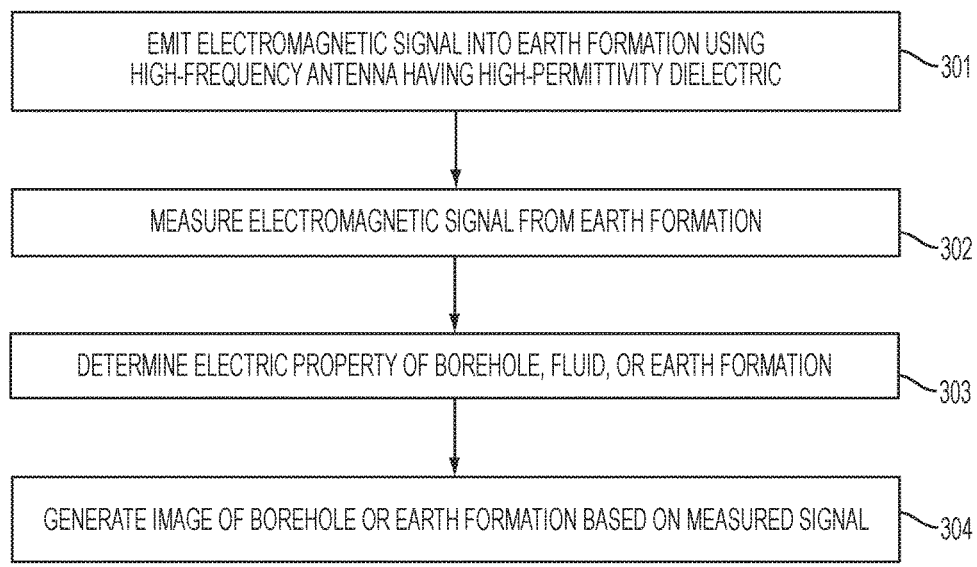
FIG. 3 is a flow diagram of a method of operating the sensor system according to an embodiment of the invention.

FIG. 3 is a flow diagram of a method according to an embodiment of the invention. In block 301, an electromagnetic signal is emitted into an earth formation from an antenna in a borehole. The antenna is a high-frequency antenna mounted on a ceramic having a high dielectric permittivity. In one embodiment, the antenna is a broadband spiral antenna.

In block 302, an electromagnetic signal is measured from the earth formation. In one embodiment, the electromagnetic signal is measured by the same antenna that transmitted the electromagnetic signal into the earth formation. In another embodiment, two separate antennae or arrays of antennae are used. In embodiments of the invention, the output from the antenna measuring the electromagnetic signal is one of a voltage, a current, and an impedance. In other words, a processing circuit may detect the voltage, current, and/or impedance at the output of the antenna to obtain data about the electromagnetic signal.

In block 303, an electric property of one or more of the borehole, a borehole fluid, and the earth formation are determined based on the measured electromagnetic signal. In block 304, an image of one or both of the borehole and the earth formation are generated based on the measured electromagnetic signal.

While one or more embodiments have been shown and described, modifications and substitutions may be made thereto without departing from the spirit and scope of the invention. Accordingly, it is to be understood that the present invention has been described by way of illustrations and not limitation.

The invention claimed is:

1. A method for determining at least one electrical property of an earth formation, comprising:
   emitting, by a first antenna, an electromagnetic signal into the earth formation;
   measuring, by a second antenna, an electromagnetic signal from the earth formation, at least one of the first and second antenna being a broadband log antenna mounted on a substrate having a at least a high dielectric permittivity, defined as a dielectric permittivity of at least about $\varepsilon=200$, or a gigantic dielectric permittivity, defined as a dielectric permittivity of about $\varepsilon=1000$ or greater, and the at least one of the first and second antenna having the high dielectric permittivity further having a radius of between about 2.5 millimeters (mm) and about 10 centimeters (cm);
   determining at least one electrical property of one or more of a borehole, a borehole fluid, and the earth formation based on measuring the electromagnetic signal,
   determining a dielectric constant of the earth formation; and
   selecting the dielectric permittivity of the substrate to be at least as high as the dielectric constant of the earth formation.

2. The method of claim 1, wherein the dielectric permittivity of the substrate is selected to be greater than the dielectric constant of the earth formation.

3. The method of claim 1, wherein the dielectric permittivity of the substrate is selected such that the at least one first and second antenna operates in a range between about 10 MHz and 30 GHz, and each of the height and width of the at least one first and second antenna is in a range between about 2 cm and about 10 cm.

4. The method of claim 1, wherein the at least one of the first and second antenna is a spiral log antenna.

5. The method of claim 1, wherein determining the at least one electrical property includes determining each of an electrical conductivity and a dielectric permittivity of the earth formation.

6. The method of claim 1, further comprising:
   generating image data based on determining the at least one electrical property.

7. The method of claim 6, wherein generating the image data includes generating 3-dimensional (3D) image data for generating a 3D image of one or more of the borehole and earth formation on a display.

8. The method of claim 1, wherein the at least one first and second antenna is an array of antennae.

9. A borehole system, comprising:
   a downhole assembly including at least one broadband log antenna configured to perform at least one of emitting an electromagnetic signal into an earth formation and measuring an electromagnetic signal from the earth formation, the at least one broadband log antenna mounted on a substrate having at least a high dielectric permittivity, defined as a dielectric permittivity of at least about $\varepsilon=200$, or a gigantic dielectric permittivity, defined as a dielectric permittivity of about $\varepsilon=1000$ or greater, and the at least one antenna further having a radius of between about 2.5 millimeters (mm) and about 10 centimeters (cm); and
   a computer configured to perform at least one of generating a signal to cause the at least one antenna to emit the electromagnetic signal into the earth formation, and receiving a signal from the antenna based on an electromagnetic signal received by the antenna from the earth formation, the computer further configured to determine at least one electrical property of one or more of a borehole, a borehole fluid, and the earth formation based on measuring the electromagnetic signal received from the at least one antenna,
   wherein the downhole assembly includes a housing including a cavity in which the substrate and antenna are housed, the housing having a conical shape having a peak around a center of the antenna, the substrate filling a space between the housing and the at least one antenna.

10. The borehole system of claim 9, wherein the antenna is a spiral log antenna.

11. The borehole system of claim 9, wherein the downhole assembly includes one of a wireline assembly, drill pipe, and a drill bit, and
   the antenna and substrate are located in the at least one of the wireline assembly, drill pipe, and a drill bit.

12. The borehole system of claim 9, wherein the substrate has a dielectric permittivity selected to be at least as high as a dielectric constant of the earth formation.

13. The borehole system of claim 9, wherein the dielectric permittivity of the substrate is such that the at least one antenna operates in a range between about 10 MHz and about 30 GHz, and each of the height and width of the at least one antenna is in a range between about 2 cm and about 10 cm.

14. A borehole system, comprising:
   a downhole assembly including at least one broadband log antenna configured to perform at least one of emitting an electromagnetic signal into an earth formation and measuring an electromagnetic signal from the earth formation, the at least one broadband log antenna mounted on a substrate having a dielectric permittivity selected to be at least as high as a dielectric constant of the earth formation, and the at least one antenna further having a radius of between about 2.5 millimeters (mm) and about 10 centimeters (cm); and
   a computer configured to perform at least one of generating a signal to cause the at least one antenna to emit the electromagnetic signal into the earth formation, and receiving a signal from the antenna based on an electromagnetic signal received by the antenna from the earth formation, the computer further configured to determine at least one electrical property of one or more of a borehole, a borehole fluid, and the earth formation based on measuring the electromagnetic signal received from the at least one antenna.

15. The borehole system of claim 14, wherein the downhole assembly includes a housing including a cavity in which the substrate and antenna are housed, the housing having a conical shape having a peak around a center of the antenna, the substrate filling a space between the housing and the at least one antenna.

16. The borehole system of claim 14, wherein the antenna is a spiral log antenna.

17. The borehole system of claim 14, wherein the downhole assembly includes one of a wireline assembly, drill pipe, and a drill bit, and the antenna and substrate are located in the at least one of the wireline assembly, drill pipe, and a drill bit.

18. The borehole system of claim 14, wherein the dielectric permittivity of the substrate is such that the at least one antenna operates in a range between about 10 MHz and about 30 GHz, and each of the height and width of the at least one antenna is in a range between about 2 cm and about 10 cm.

\* \* \* \* \*